(12) United States Patent  (10) Patent No.: US 9,327,045 B2
Bourne  (45) Date of Patent: May 3, 2016

(54) AIR FRESHENER WITH POROUS MEMBRANE WITH LEAK PAD AND ADJUSTABLE OPENING

(71) Applicant: American Covers, Inc., Draper, UT (US)

(72) Inventor: Chris Bourne, Standsbury Park, UT (US)

(73) Assignee: American Covers, Inc., Draper, UT (US)

( * ) Notice: Subject to any disclaimer, the term of this patent is extended or adjusted under 35 U.S.C. 154(b) by 218 days.

(21) Appl. No.: 14/060,127

(22) Filed: Oct. 22, 2013

(65) Prior Publication Data

US 2015/0108239 A1  Apr. 23, 2015

(51) Int. Cl.
*A61L 9/12* (2006.01)
*B60H 3/00* (2006.01)

(52) U.S. Cl.
CPC . *A61L 9/12* (2013.01); *A61L 9/127* (2013.01); *B60H 3/0028* (2013.01); *A61L 2209/131* (2013.01)

(58) Field of Classification Search
CPC . A61L 9/12; A61L 2209/13; A61L 2209/131; B60H 3/0028
USPC ................................................. 239/6, 34–60
See application file for complete search history.

(56) References Cited

U.S. PATENT DOCUMENTS

| 3,727,840 | A |   | 4/1973 | Nigro |
| 3,908,906 | A | * | 9/1975 | Crowle ..................... A61L 9/12 239/58 |
| 4,378,819 | A |   | 4/1983 | Macho |
| 4,890,791 | A | * | 1/1990 | Hoffman .................. A61L 9/127 239/326 |
| 4,947,578 | A |   | 8/1990 | Anderson et al. |
| 5,014,913 | A | * | 5/1991 | Hoyt ......................... A61L 9/12 239/45 |
| 5,439,100 | A | * | 8/1995 | Gordon ..................... A61L 9/12 206/204 |
| 5,752,658 | A | * | 5/1998 | Gibbs ....................... A61L 9/12 16/442 |
| 5,868,315 | A | * | 2/1999 | Chen ......................... A61L 9/12 239/34 |
| 5,875,968 | A |   | 3/1999 | Miller et al. |
| 6,050,551 | A | * | 4/2000 | Anderson ............... A61L 9/122 239/56 |
| 7,070,172 | B2 | * | 7/2006 | Fabrega .............. A01M 1/2033 239/59 |
| 7,273,184 | B2 | * | 9/2007 | Brown ................ A01M 1/2044 220/87.1 |
| 7,530,503 | B2 | * | 5/2009 | Caserta ............... A01M 1/2044 239/34 |
| 7,708,256 | B2 | * | 5/2010 | Pankhurst ................ A61L 9/02 261/104 |
| 7,980,486 | B2 | * | 7/2011 | Trent .................. A01M 1/2055 206/484.1 |

(Continued)

*Primary Examiner* — Ryan Reis
*Assistant Examiner* — Joseph A Greenlund
(74) *Attorney, Agent, or Firm* — Thorpe, North & Western, LLP (57) ABSTRACT

An air freshener comprises a scent capsule carried by a housing. The scent capsule comprises a reservoir containing a fragrant material, and with an opening to a cavity therein and covered by a permeable membrane through which a fragrance can permeate, and a releasable seal sealed over the opening and the permeable membrane to resist fragrance release until removed. An absorptive pad is disposed behind the releasable seal between the scent capsule and the housing, and is capable of absorbing the fragrant material that permeates through the permeable membrane.

19 Claims, 9 Drawing Sheets

(56) References Cited

U.S. PATENT DOCUMENTS

| | | | | |
|---|---|---|---|---|
| 8,062,598 B2 * | 11/2011 | Bertassi | A01M 1/2044 239/58 |
| 8,251,299 B1 * | 8/2012 | Irvin | A61L 9/048 220/23.83 |
| 8,367,011 B2 * | 2/2013 | Yamamoto | A01M 1/2033 239/53 |
| 8,485,454 B1 * | 7/2013 | Irvin | A61L 9/125 239/34 |
| 8,647,587 B2 * | 2/2014 | Dunn | B65F 1/062 220/522 |
| 2003/0190255 A1 | 10/2003 | Boden et al. | |
| 2005/0127538 A1 | 6/2005 | Fabrega et al. | |
| 2006/0104868 A1 * | 5/2006 | Saxon | A01K 15/02 422/125 |
| 2007/0001023 A1 * | 1/2007 | Green | A61L 9/12 239/34 |
| 2008/0099576 A1 * | 5/2008 | Hart | A61L 9/12 239/53 |
| 2010/0314461 A1 * | 12/2010 | Gruenbacher | A61L 9/12 239/6 |
| 2012/0153038 A1 * | 6/2012 | Willert | 239/34 |
| 2014/0076989 A1 * | 3/2014 | Granger | A61L 9/12 239/52 |
| 2014/0314649 A1 * | 10/2014 | Zhou | B01D 53/007 423/239.2 |

* cited by examiner

AIR FRESHENER WITH POROUS MEMBRANE WITH LEAK PAD AND ADJUSTABLE OPENING

BACKGROUND

1. Field of the Invention

The present invention relates generally to air fresheners.

2. Related Art

Air fresheners can be used to provide an aesthetically pleasing scent in a desired area. One type of air freshener utilizes a fragrant material that permeates through a permeable membrane. During storage and prior to use, the fragrant material and the permeable membrane can be sealed by a foil liner or cover. Prior to use, the liner or cover is removed to expose the membrane and allow the fragrant material to permeate through the membrane.

SUMMARY OF THE INVENTION

It has been recognized that it would be advantageous to develop an air freshener to provide a desired scent. In addition, it has been recognized that fragrant material can permeate the permeable membrane and pool between the membrane and the liner or cover, to leak from the air freshener as the liner or cover is removed. Furthermore, it has been recognized that it would be advantageous to develop an air freshener that resists spilling or leaking of fragrant material, even pools of fragrant material that build up or pool between a permeable membrane and a liner or cover prior to use.

The invention provides an air freshener comprising a scent capsule carried by a housing. The scent capsule comprises a reservoir containing a fragrant material. An opening to a cavity in the scent capsule is covered by a permeable membrane through which a fragrance can permeate. A releasable seal is sealed over the opening and the permeable membrane to resist fragrance release until removed. An absorptive pad is disposed behind the releasable seal, between the scent capsule and the housing, and is capable of absorbing the fragrant material that permeates through the permeable membrane.

In accordance with a more detailed aspect of the invention, the housing can comprise a pair of shells pivotally coupled together at a rocker hinge defining a rocker axis, and substantially separated from one another by a gap therebetween. The rocker axis can be off-center with respect to the pair of shells, and can divide each of the pair of shells at the rocker axis into a long lobe and a short lobe. The pair of shells can rock about the rocker axis between: i) a low position in which the long lobes of the pair of shells are pivoted substantially together and separating the short lobes of the pair of shell from one another to substantially narrow the gap between the long lobes corresponding to a low scent release; and ii) a high position in which the short lobes of the pair of shells are pivoted substantially together and separating the long lobes of the pair of shells from one another to substantially widen the gap between long lobes corresponding to a high scent release.

In addition, the invention provides an air freshener with a housing comprising a pair of shells pivotally coupled together at a rocker hinge defining a rocker axis, and substantially separated from one another by a gap therebetween. The rocker axis is off-center with respect to the pair of shells, and divides each of the pair of shells at the rocker axis into a long lobe and a short lobe. One of the pair of shells defines an outer shell with an aperture therein; while one of the pair of shells defining an inner shell. An arc wall is formed around at least a portion of the aperture on an interior of the outer shell and defines a pocket. A scent capsule is carried by the housing, and comprises a reservoir containing a fragrant material. An opening to a cavity in the vessel is covered by a permeable membrane through which a fragrance can permeate. A releasable seal is sealed over the opening and the permeable membrane to resist fragrance release until removed. The scent capsule has a vessel defining the cavity, and a perimeter flange circumscribing the vessel and the cavity. The vessel of the capsule is disposed in the aperture of the outer shell with the perimeter flange abutting the outer shell in the pocket and at least partially surrounded by the arc wall. An absorptive pad is disposed behind the releasable seal and is capable of absorbing the fragrant material that permeates through the permeable membrane. A retainer ring is disposed against the absorptive pad and holds the scent capsule and the absorptive pad in the pocket. The retainer ring is at least partially surrounded by the arc wall. The absorptive pad is annular with an aperture therein. The absorptive pad has a perimeter aligned with a perimeter of the reservoir. The absorptive pad comprises an absorptive material that is fibrous and porous. The pair of shells have opposing, spaced-apart inner rims. The rim of at least one of the shells forming a pair of portions about the rocker axis with a long rim associated with the long lobe and a short rim associated with the short lobe. The long and short rims form an obtuse angle. The pair of shells rock about the rocker axis between: i) a low position in which the long lobes of the pair of shells are pivoted substantially together and separate the short lobes of the pair of shell from one another to substantially narrow the gap between the long lobes corresponding to a low scent release, and ii) a high position in which the short lobes of the pair of shells are pivoted substantially together and separate the long lobes of the pair of shells from one another to substantially widen the gap between the long lobes corresponding to a high scent release.

Furthermore, the invention provides an air freshener comprising a housing with a pair of shells pivotally coupled together at a rocker hinge to define a rocker axis, and substantially separated from one another by a gap therebetween. A fragrant material is disposed in the housing between the pair of shells. The rocker axis is off-center with respect to the pair of shells, and divides each of the pair of shells at the rocker axis into a long lobe and a short lobe. The pair of shells rock about the rocker axis between i) a low position in which the long lobes of the pair of shells are pivoted substantially together and separate the short lobes of the pair of shell from one another to substantially narrow the gap between the long lobes corresponding to a low scent release, and ii) a high position in which the short lobes of the pair of shells are pivoted substantially together and separate the long lobes of the pair of shells from one another to substantially widen the gap between the long lobes corresponding to a high scent release.

BRIEF DESCRIPTION OF THE DRAWINGS

Additional features and advantages of the invention will be apparent from the detailed description which follows, taken in conjunction with the accompanying drawings, which together illustrate, by way of example, features of the invention; and, wherein.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENT(S)

Definitions

The term "scent material" and "fragrant material" are used interchangeably herein to refer broadly to a material that carries a desired fragrance or scent, or even a neutralizing agent. The fragrant material can be a liquid, such as a scented oil.

Description

As illustrated in FIGS. 1-24, an air freshener, indicated generally at 10, in an example implementation in accordance with the invention is shown. The air freshener can be utilized to provide and aesthetically pleasing scent and/or neutralizing agent in a desired area, such as a vehicle. In a vehicle the air freshener can be secured or held by louvers of an air vent or a sun visor. The air freshener 10 can be used with a scent capsule with a releasable seal covering a permeable membrane prior to use. The air freshener can resist leaking or spilling of a fragrant material, including an amount of fragrant material that permeates through the permeable membrane and accumulates between the permeable membrane and the releasable seal defining a leak pool of fragrant material. In addition, the air freshener 10 can provide a simple and adjustable scent release.

The air freshener 10 comprises a scent capsule 14 carried by a housing 18. The housing 18 can comprise a pair of shells, including a front and/or outer shell 22, and a rear and/or inner shell 24. The shells can be or can have outer discs or plates with cavities that face one another. The scent capsule can be disposed in the cavities of the shells and between the shells. The desired scent from the scent capsule can escape from between the plates around a perimeter of the air freshener. In addition, or in the alternative, the desired scent from the scent capsule can escape through holes in the housing. The pair of shells, or outer and inner shells 22 and 24, is pivotally coupled together at a rocker hinge 28 defining a rocker axis 32. The pair of shells, or outer and inner shells 22 and 24, is substantially separated from one another by a gap 36 therebetween, around at least a portion of an outer perimeter of each shell. The gap 36 can extend around at least a portion of, or an entirety of, a lateral perimeter of the air freshener or housing or shells, to allow release of scent from the housing. The pair of shells can pivot or rock about the rocker axis 32 to vary a width and/or location of the gap to control and alter the scent release, as discussed in greater detail below.

The rocker axis 32 can be off-center with respect to the pair of shells 22 and 24. In addition, the rocker axis 32 can divide each of the pair of shells at the rocker axis into a long lobe and a short lobe. Thus, the outer shell 22 can have a long lobe 40 extending from the rocker axis 32 in one direction, and a short lobe 42 extending from the rocker axis 32 in another opposite direction. The long lobe 40 can be longer than the short lobe 42. Similarly, the inner shell 24 can have a long lobe 44 extending from the rocker axis 32 in one direction, and a short lobe 48 extending from the rocker axis 32 in another opposite direction. The long lobe 44 can be longer than the short lobe 48. The long lobes 40 and 44 can be aligned with one another, and can oppose one another. Similarly, the short lobes 42 and 48 can be aligned with one another, and can oppose one another. The rocker axis 32 can separate or divide the gap 36 into a long gap 50 corresponding to the long lobes, and a short gap 52 corresponding to the short lobes. The pair of shells can pivot or rock about the rocker axis to substantially or somewhat selectively close and open the long and short gaps.

In addition, the pair of shells 22 and 24 can have opposing, spaced-apart inner rims and facing edges. The gap 36 between the pair of shells can be defined between the rims of the shells. The rim of at least one of the shells can form an angle about the rocker axis 32. For example, the rim can have two portions or two linear portions, such as a long linear rim 56, corresponding to the long lobe, and a short linear rim 58, corresponding to the short lobe. The angle formed between the two portions of the rim can be an obtuse angle. Thus, the gap on one side of the pivot axis 32 can be wider than on an opposite side. The gap between the long lobes can be greater or have a greater opening size relative to the gap between the short lobes, due to the off-center rocker axis to control and vary scent release. The wider gap can be selectively alternated between the opposite sides of the rocker axis 32 to control and alter the scent release.

The outer shell 22 can be annular with an aperture 60 therethrough. The aperture 60 can be centered in the outer shell. The outer shell 22 can have an outer surface or exterior with indicia. In addition, the outer shell 22 can have an interior. An annular flange 62 can extend around the aperture 60, and can extend inwardly from the exterior. In addition, an arc wall 64 can be formed around at least a portion of the aperture 60 and the annular flange 62 on the interior of the outer shell. The arc wall can extend inwardly. The arc wall 64 can define a pocket 68 at the aperture. The aperture and annular flange can also define the pocket along with the arc wall. The arc wall 64 can include a pair of tabs 72 on the arc wall opposite one another across the pocket. The tabs can include an aperture for an axel of the rocker hinge.

As described above, the air freshener 10 includes a scent capsule 14 carried by the housing 18. Specifically, the scent capsule 14 can be carried by the outer shell 22, and between the outer and inner shells 22 and 24. Furthermore, the scent capsule 14 can be disposed in the pocket 68 of the outer shell 22.

The scent capsule 14 comprises a reservoir 78 containing a fragrant material 82. The fragrant material 82 can be a liquid or oil with a desired fragrance or scent, and a desired color that can correspond to the fragrance or scent. The reservoir 78 can comprise a bowl or vessel 86 with a cavity therein and a perimeter flange 90 circumscribing the vessel and the cavity. The reservoir and/or vessel can be formed by or can include a sheet, such as a transparent or translucent plastic, indented on one side to form the reservoir or vessel circumscribed by a rim or perimeter flange. The reservoir and/or vessel or cavity thereof can be formed by vacuum forming the plastic sheet, and die cutting the reserovoir or vessel from the vacuum formed plastic sheet. The reservoir and/or vessel with the cavity therein can be formed by or defined by the plastic sheet with an indentation therein forming the cavity circumscribed by a rim or perimeter flange. The indentation in the plastic sheet forms the cavity on one side of the sheet, and a protrusion on the opposite side of the sheet that is defined by and matches the indentation on the opposite side. Thus, the indentation and protrusions are on opposite sides of the sheet, and the capsule. The protrusion can define a front of the capsule or vessel, while the indentation can define a rear of the capsule or vessel. The capsule or vessel or protrusion has a front surface. The plastic sheet defines a capsule or vessel wall with a substantially constant thickness, and the plastic sheet or wall can be transparent or at least translucent, or have a portion thereof that is transparent or translucent. The scent capsule 14 and/or the reservoir 78, or the protrusion thereof, can be disposed in the aperture 60 of the outer shell 22 with the perimeter flange 90 abutting the outer shell in the pocket 68 and at least partially surrounded by the arc wall 64. The front surface of the capsule or vessel can be substantially flush with an outer surface of the outer shell. Thus, the fragrant material 82 can be visible through the wall, and thus through the capsule and vessel, and through the outer shell. The capsule and/or the reservoir and the aperture in the shell can have matching shapes, such as a circular perimeter.

An opening to the cavity of the vessel or reservoir is covered by a permeable membrane 94 defining the vessel between the plastic sheet of the capsule and the permeable membrane. Thus, the vessel is formed by and completely enclosed by the plastic sheet and the permeable membrane. The permeable membrane can be substantially flat. The reservoir 78 can be formed by the vessel 86 and the permeable membrane 94. The permeable membrane can be adhered or welded to the perimeter flange. A fragrance of the fragrant material, and/or the fragrant material, can permeate through the permeable membrane over time. The permeable membrane can be substantially permeable to air or gas, while being substantially impermeable to liquid or oil. A releasable seal 100 is sealed over the opening and the permeable membrane 94 to resist fragrance release until removed. Thus, the releasable seal 100 is disposed over the membrane prior to use and releasable therefrom to initiate use. The seal 100 can be releasably secured to the perimeter flange 90. The releasable seal can have a tacky or adhesive surface or perimeter that adheres to the membrane or rim or perimeter flange. The releasable seal can be a foil that covers the membrane, and is temporarily sealed around its perimeter. This foil prevents the fragrance from evaporation prior to usage. When the customer receives the product, he or she can remove the foil covering the membrane to begin the scent release. A tab can extend from the releasable seal, and beyond the housing, such as between the pair of shells, to be grasped and pulled by a user in order to remove the seal from the scent capsule.

In one aspect, the rim or perimeter flange 90 of the reservoir or vessel can be stepped, with the membrane 94 affixed to an inner step, and the seal 100 releasably coupled to an outer step.

As described above, the scent capsule 14 can have the releasable seal 100 covering the permeable membrane 94 to resist leaking or spilling of the fragrant material 82. During normal use, with the releasable seal removed, such fragrant material can evaporate prior to accumulation or leaking. But prior to use, an amount of the fragrant material can permeates through the permeable membrane 94 and can accumulate between the permeable membrane and the releasable seal 100, defining a leak pool of fragrant material, prior to use, and prior to removal of the releasable seal. As a user removes the releasable seal 100, the leak pool of fragrant material can leak through the housing and the pair of shells to potentially come in contact with other surfaces. The air freshener has an absorptive pad 120 disposed behind the releasable seal 100 and the scent capsule, and capable of absorbing the fragrant material, or leak pool, that permeates through the permeable membrane. The absorptive pad 120 absorbs the leak pool of fragrant material upon removal of the releasable seal to resist the fragrant material from leaking out of the housing. Thus, the absorptive pad 120 can be disposed against, or can abut to, the releasable seal 100 prior to use. The absorptive pad can be annular, and can have at least one aperture therethrough located at an interior with respect to a perimeter of the absorptive pad. Thus, the pad can absorb the leak pool without interfering with the permeable membrane. The absorptive pad can have a perimeter aligned with a perimeter of the reservoir, or surrounding and overlapping a perimeter of the vessel or cavity. The perimeter of the absorptive pad can extend beyond, both radially outward and inward, the vessel, and can overlap the rim or annular flange. The absorptive pad 120 can comprise an absorptive material that is fibrous and porous. Thus, the fragrant material can be absorbed initially, and can evaporate over time.

A retainer ring 130 can be disposed against the absorptive pad 120, and can hold the scent capsule 14 and the absorptive pad in the pocket 68. The retainer ring 130 fits within and is at least partially surrounded by the arc wall 64. The retainer ring can be retained in the pocket by a snap-fit, friction fit, press fit and/or interference with the arc wall. The retainer ring can have tabs on opposite sides that are beveled on one side and stepped on the other to snap fit into corresponding apertures in the arc wall. The retainer ring can have an annular or circular indentation therein with a bottom flange to retain the pad in the housing and against the membrane. Thus, the retainer ring 130 can hold the scent capsule 14 and the absorptive pad 120 to the outer shell 22 of the housing. The retaining can form part of the housing along with the shells.

As described above, the outer and inner shells 22 and 24 can be pivotally coupled together at the rocker hinge 28 defining the rocker axis 32. In addition, the arc wall 64 of the outer shell 22 can have the pair of tabs 72 on the arc wall opposite one another across the pocket with an aperture for an axel of the rocker hinge. The inner shell 24 can have a pair of tabs 134 extending from the inner shell towards the outer shell, and with an aperture for the axel of the rocker hinge. The pair of tabs 72 of the outer shell can be aligned with the outer tabs 134 of the inner shell 24. An axel or pair of pins can extend through the apertures of the tab to form the rocker hinge and about which the pair of shells rock.

Figure 1:
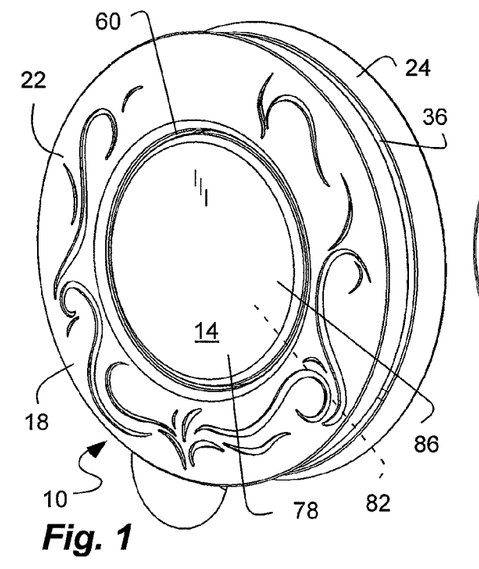
FIG. 1 is a perspective view of an air freshener in accordance with an embodiment of the present invention, shown in a low scent release position, and a storage or pre-use configuration with a releasable seal.
Figure 2:
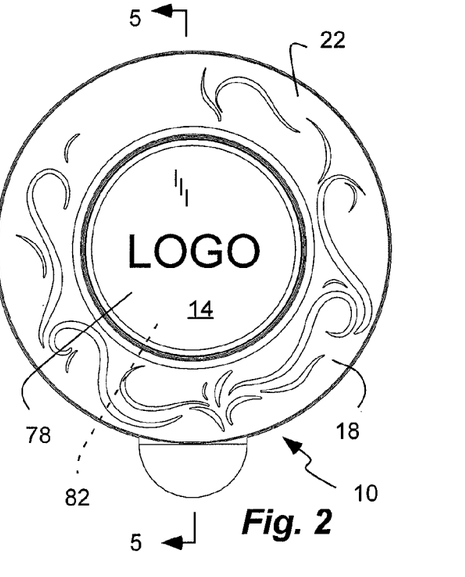
FIG. 2 is a front view of the air freshener of FIG. 1.
Figure 3:
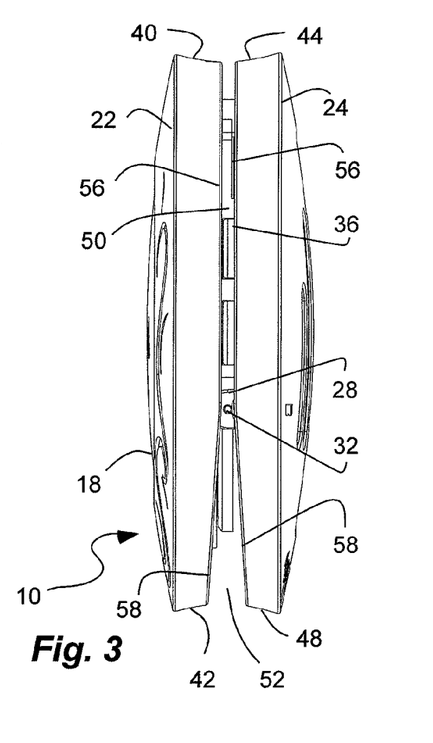
FIG. 3 is a side view of the air freshener of FIG. 1, shown in the low scent release position, and an in-use configuration with the releasable seal removed.
Figure 4:
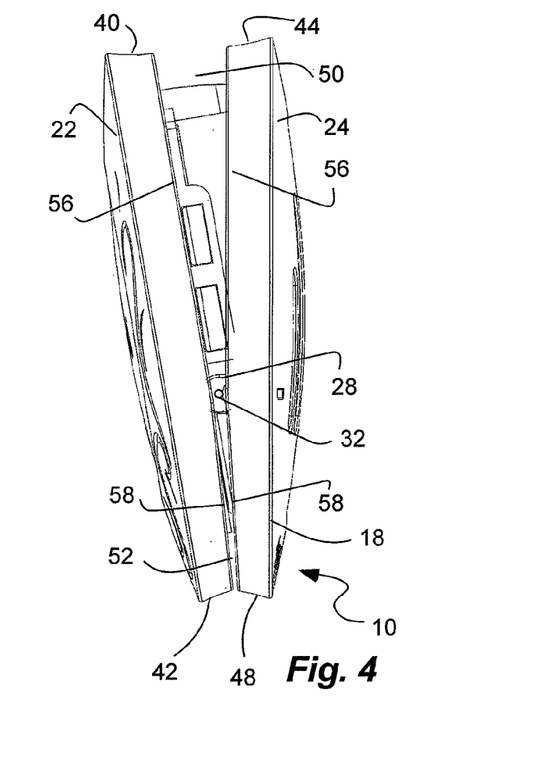
FIG. 4 is a side view of the air freshener of FIG. 1, shown in a high scent release position, and the in-use configuration.
Figure 5:
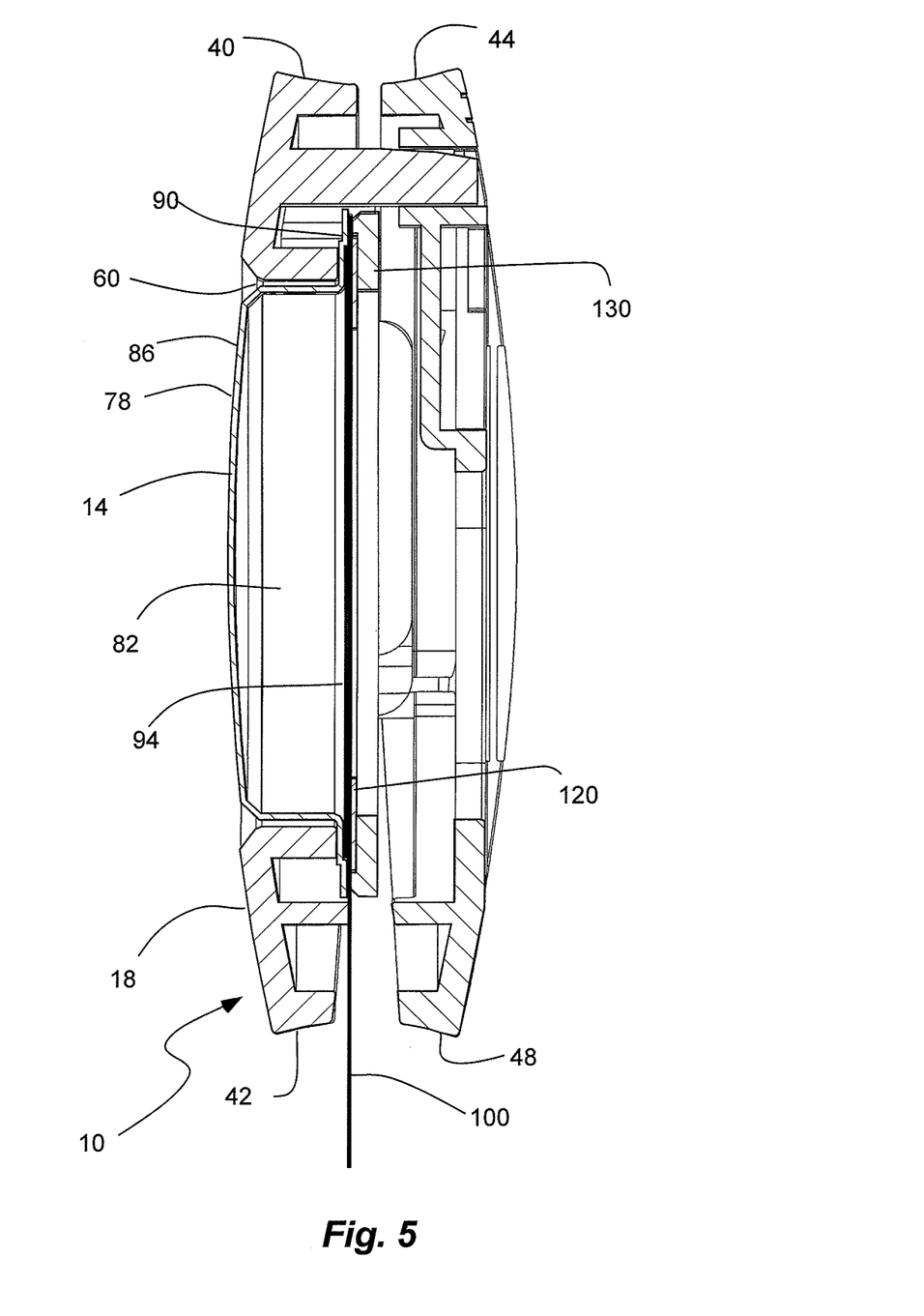
FIG. 5 is a cross-sectional side view of the air freshener of FIG. 1, taken along line 5 of FIG. 2, shown in the low scent release position, and the storage or pre-use configuration, with the releasable seal.
Figure 6:
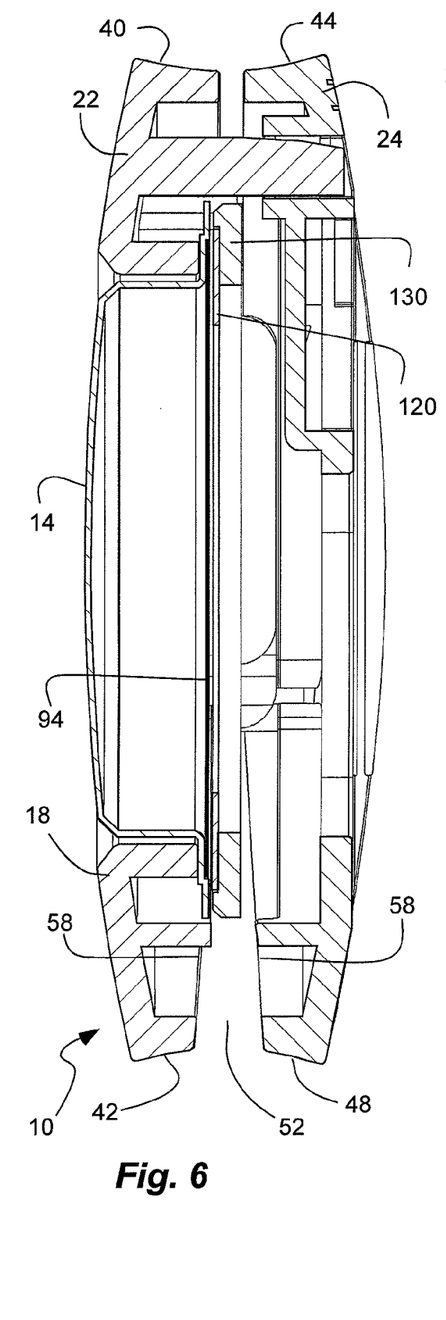
FIG. 6 is a cross-sectional side view of the air freshener of FIG. 1, shown in the lower scent release position, and the in-use configuration with the releasable seal removed.
Figure 7:
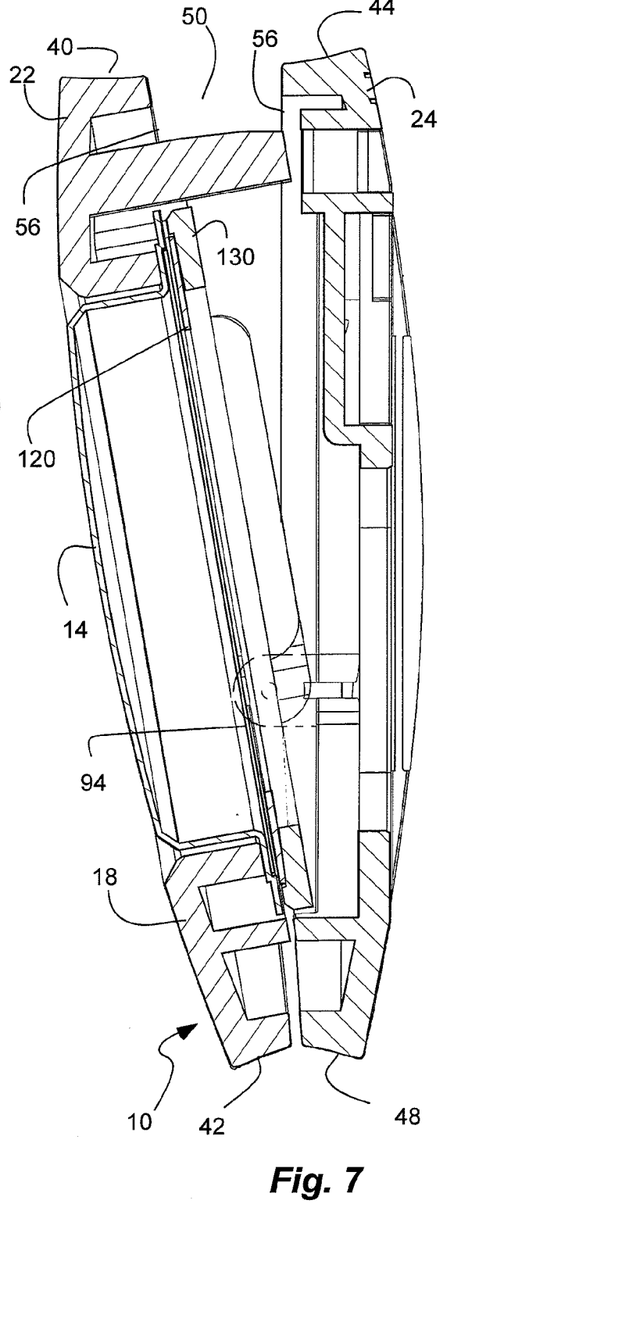
FIG. 7 is a cross-sectional side view of the air freshener of FIG. 1, shown in the higher scent release position, and the in-use configuration with the releasable seal removed.
Figures 8, 9:
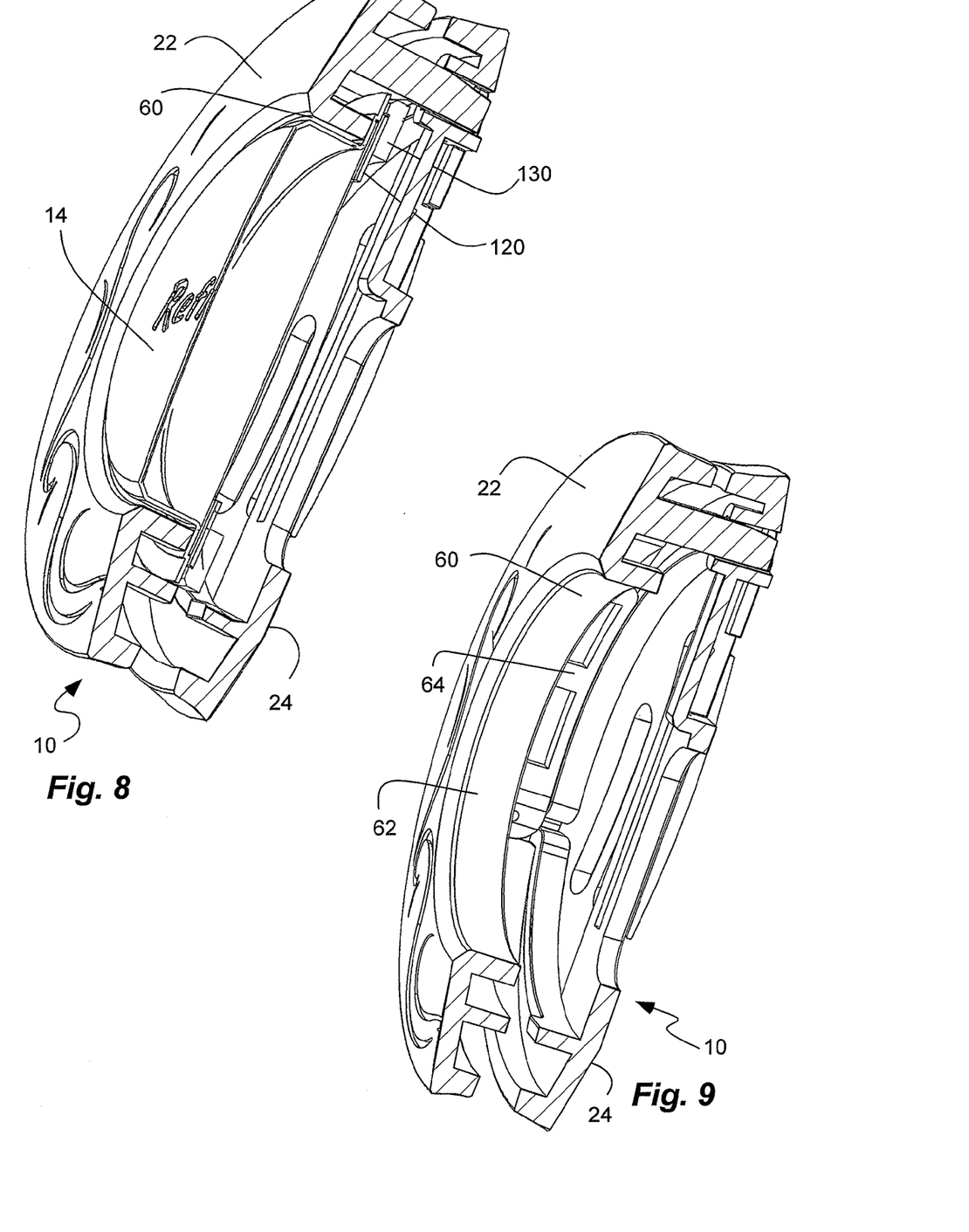
FIG. 8 is a cross-sectional perspective view of the air freshener of FIG. 1.
FIG. 9 is a cross-sectional perspective view of the air freshener of FIG. 1, shown with only a pair of shells of a housing and with a scent capsule and a retaining ring removed.
Figures 10, 11:
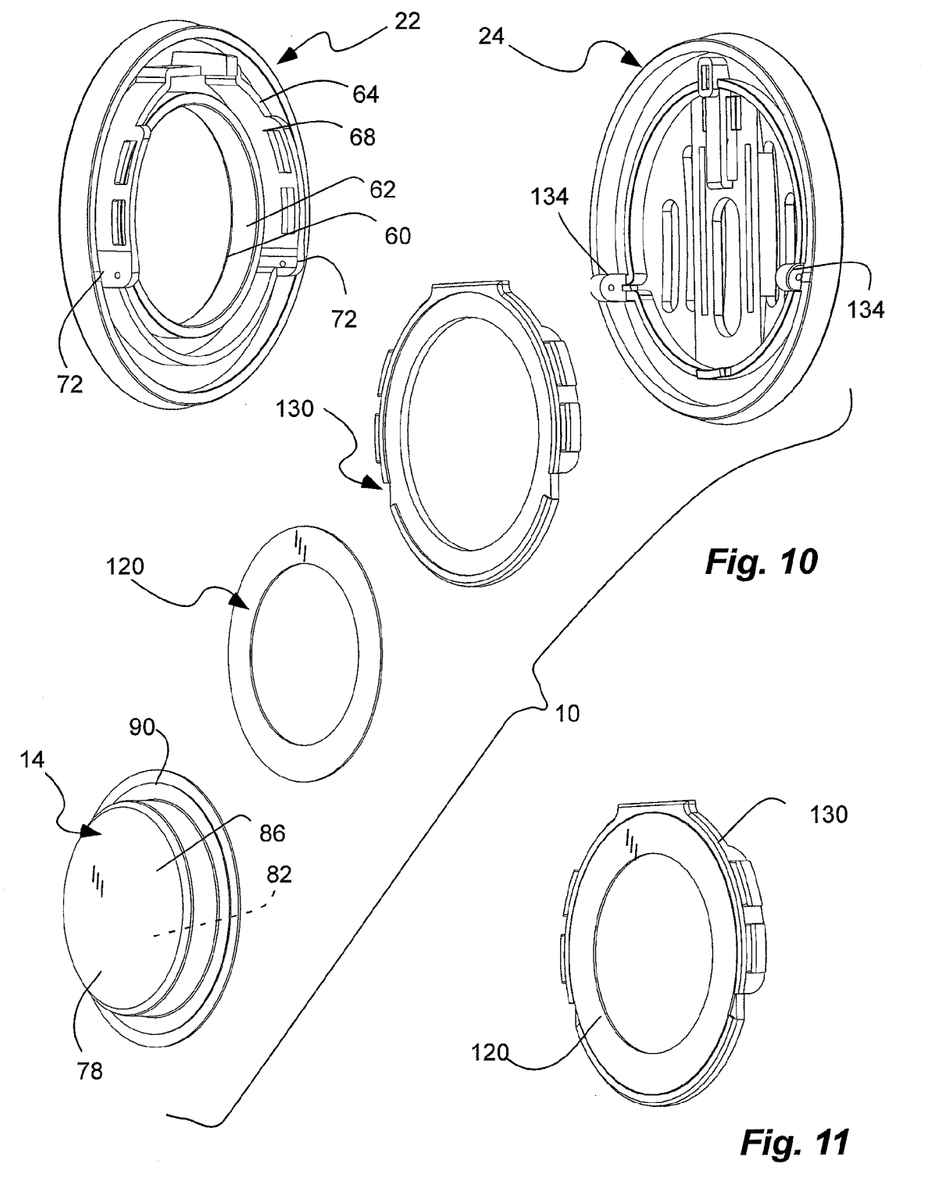
FIG. 10 is an exploded perspective view of the air freshener of FIG. 1.
FIG. 11 is a perspective view of the retaining ring and absorptive pad of FIG. 1.
Figure 12:
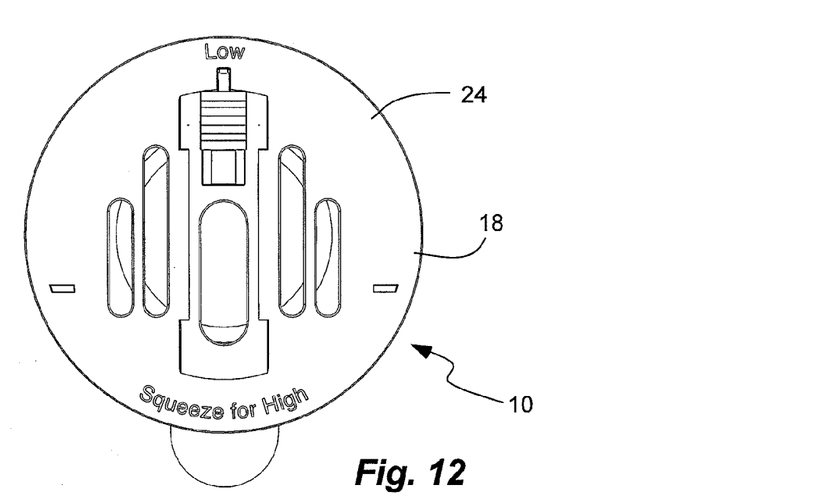
FIG. 12 is a rear view of the air freshener of FIG. 1.

As described above, the rocker axis 32 can be off-center with respect to the pair of shells, and can divide each of the pair of shells at the rocker axis into long lobes 40 and 44 and a short lobes 42 and 48. The pair of shells 22 and 24 rocks about the rocker axis 32 between a low position (FIGS. 3 and 6) and a high position (FIGS. 4 and 7). In the low position, the long lobes 40 and 44 of the pair of shells 22 and 24 pivot substantially together, and the short lobes 42 and 48 of the pair of shell are separated (relatively) from one another, to substantially narrow the gap 56 between the long lobes and widen the gap 52 between the short lobes, corresponding to a low scent release. In the high position, the short lobes 42 and 48 of the pair of shells are pivoted substantially together, and the long lobes 40 and 44 of the pair of shells are separated (relatively) from one another, to substantially widen the gap 56 between the long lobes, and narrow the gap 52 between the short lobes, corresponding to a high scent release. As described above, the shells can have an obtuse angle formed between the two portions of the rim to form a wider gap on one side of the pivot axis 32 than on an opposite side. The gap between the long lobes can be greater or have a greater opening size relative to the gap between the short lobes, due to the off-center rocker axis to control and vary scent release. The wider gap can be selectively alternated between the opposite sides of the rocker axis 32 to control and alter the scent release.

Figure 13:
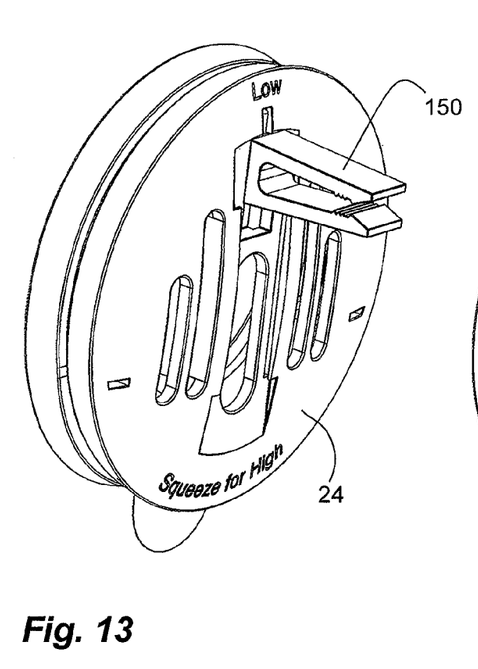
FIG. 13 is a rear perspective view of the air freshener of FIG. 1, shown with a vent clip.
Figure 14:
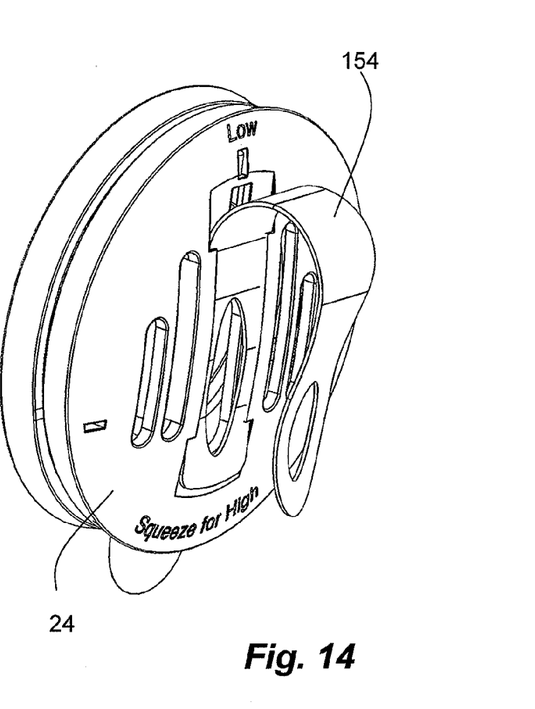
FIG. 14 is a rear perspective view of the air freshener of FIG. 1, shown with a visor clip.
Figure 15:
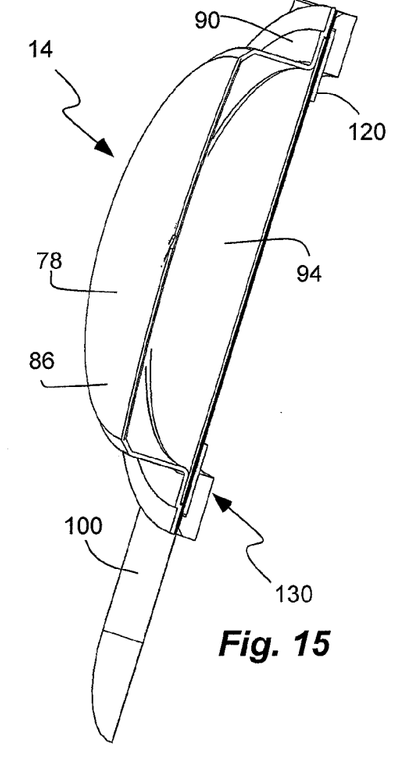
FIG. 15 is a cross-sectional perspective view of the scent capsule, the release seal, the absorptive pad, and the retaining ring of the air freshener of FIG. 1.
Figure 16:
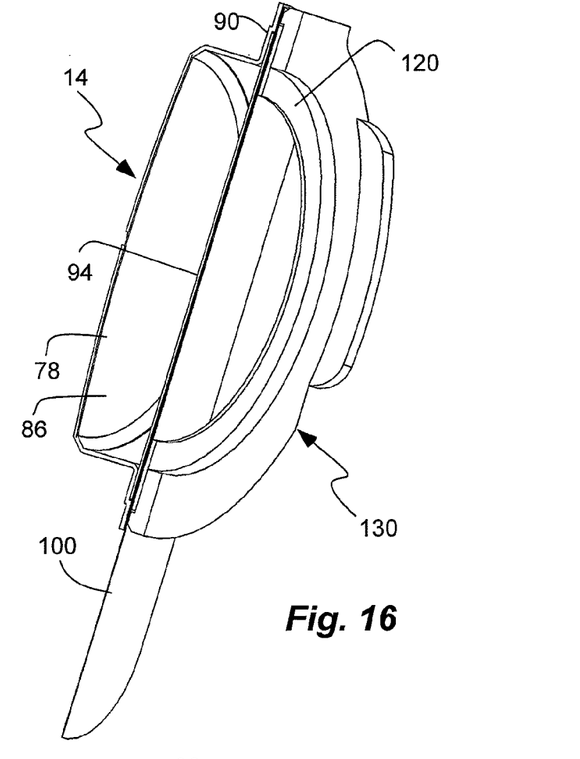
FIG. 16 is a cross-sectional perspective view of the scent capsule, the release seal, the absorptive pad, and the retaining ring of the air freshener of FIG. 1.
Figures 17, 18:
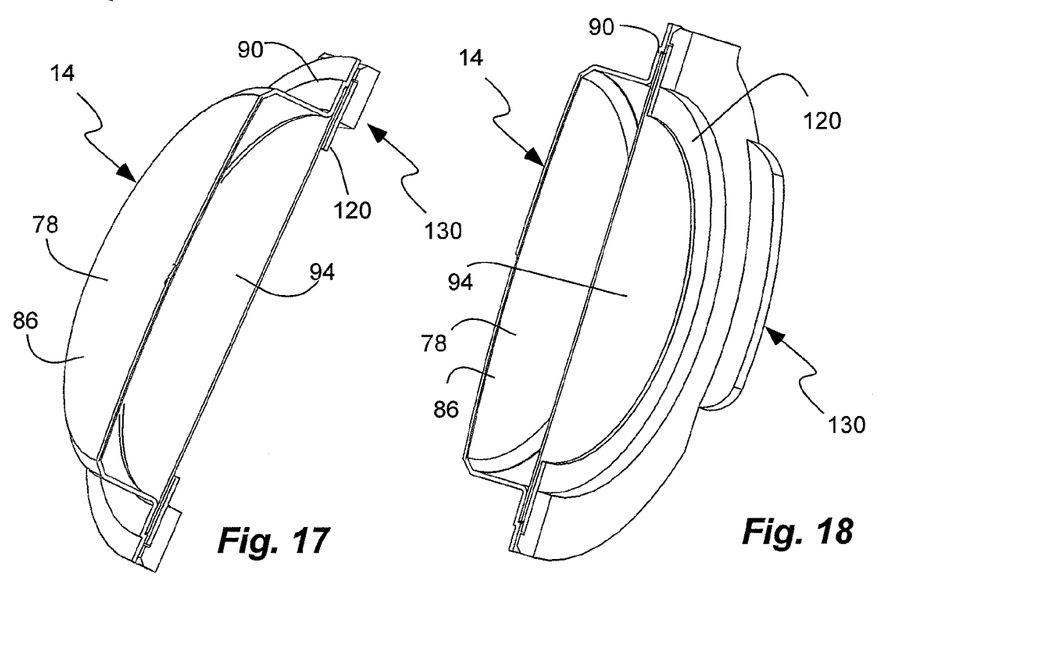
FIG. 17 is a cross-sectional perspective view of the scent capsule, the absorptive pad, and the retaining ring of the air freshener of FIG. 1, with the release seal removed.
FIG. 18 is a cross-sectional perspective view of the scent capsule, the absorptive pad, and the retaining ring of the air freshener of FIG. 1, with the release seal removed.
Figures 19, 20, 21:
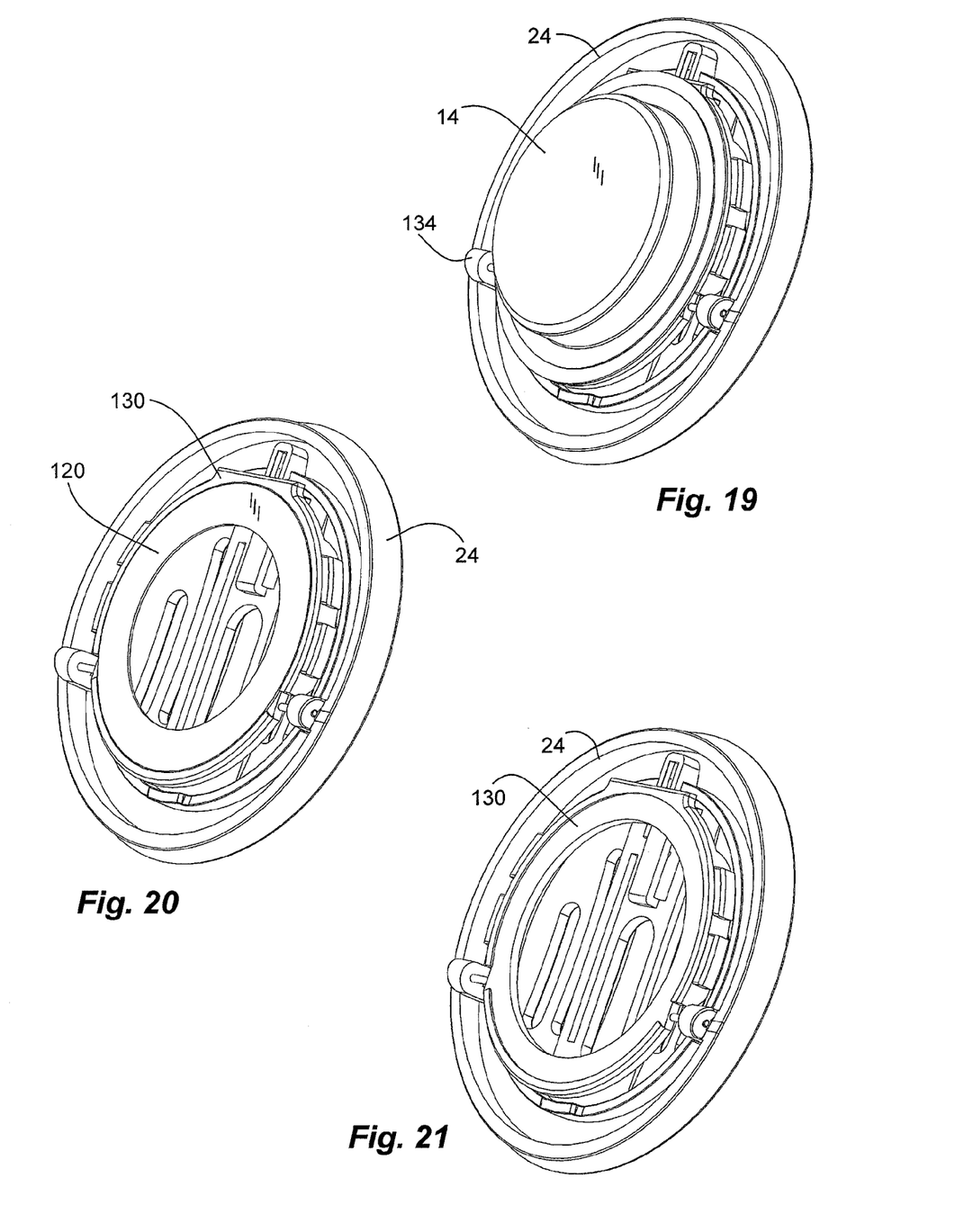
FIG. 19 is a perspective view of the air freshener of FIG. 1, shown with an outer shell and the release seal removed.
FIG. 20 is a perspective view of the air freshener of FIG. 1, shown with an outer shell, the scent capsule and the release seal removed to reveal the absorptive pad.
FIG. 21 is a perspective view of the air freshener of FIG. 1, shown with an outer shell, the scent capsule, the absorptive pad and the release seal removed to reveal the retaining ring and an inner shell of the housing.
Figure 22:
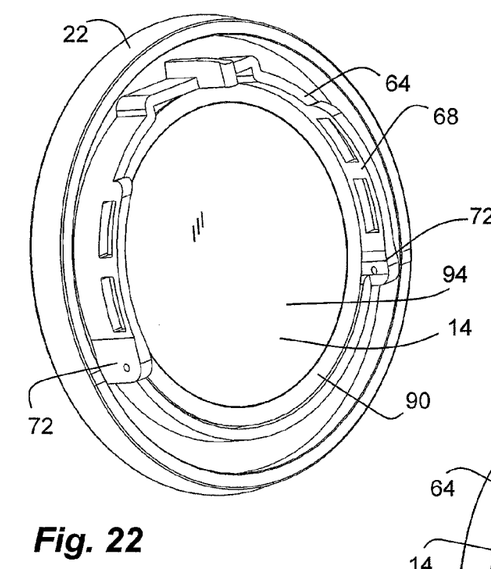
FIG. 22 is a perspective view of the outer shell of the housing of the air freshener of FIG. 1.
Figure 23:
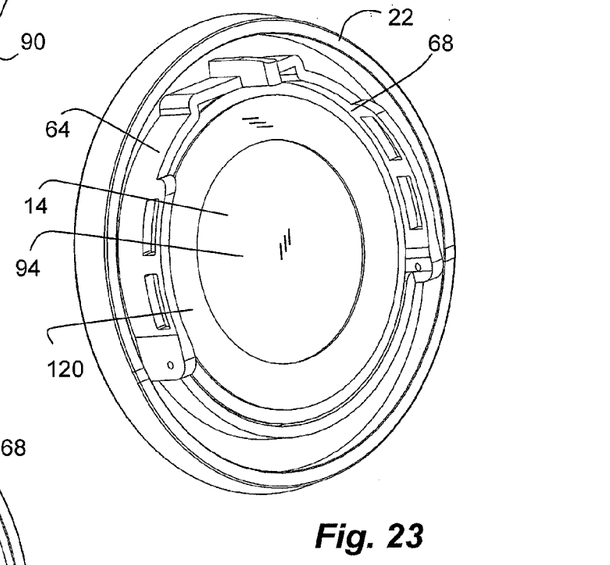
FIG. 23 is a perspective view of the outer shell of the housing and the absorptive pad of the air freshener of FIG. 1.
Figure 24:
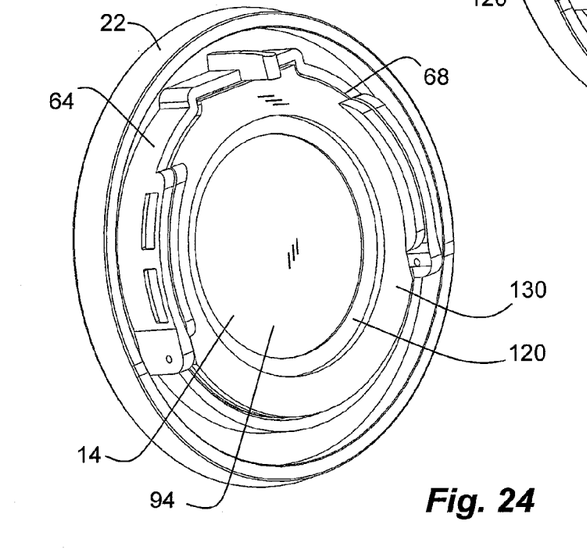
FIG. 24 is a perspective view of the air freshener of FIG. 1, shown with the inner shell of the housing and the scent capsule removed to reveal the retaining ring and absorptive pad.

In one aspect, the air freshener 10 and/or the housing 18 and/or the pair of shells 22 and 24 can be oriented substantially vertically, with the front facing substantially horizontally or outwardly. The inner shell 24 can be configured to receive a vent clip 150, as shown in FIG. 13, to clip to a louver of an air vent of a vehicle. In another aspect, the air freshener 10 and/or the housing 18 and/or the pair of shells 22 and 24 can be oriented substantially horizontally, with the front facing substantially vertically or downwardly. The inner shell 24 can be configured to receive a visor clip 155, as shown in FIG. 14, to clip to a visor of a vehicle. The vent clip and the visor clip are examples of mounting means attached to the inner shell for mounting the housing to a support surface.

In use, the releasable seal is removed from the scent capsule with the absorptive pad held against the permeable membrane or a perimeter flange of the scent capsule or both. The upper lobes of the pair of shells are pushed together to decrease an amount of scent released. The lower lobes of the pair of shells are pushed together to increase an amount of scent released. In one aspect, the lobes can be pinched between the user's fingers. In another aspect, the long lobe 40 of the outer shell 22 can be pressed inward (towards the air vent or visor) for less scent; while the short lobe 42 of the outer shell can be pressed inward for more scent.

The vessel or capsule, or plastic sheet or wall thereof, can be transparent or translucent, and the fragrant material can have a color so that the fragrant material is visible through the transparent or translucent vessel or capsule, or wall thereof. In one aspect the fragrant material is scented oil. In another aspect, the fragrant material is a scented gel. In one aspect, the fragrant material is at least translucent. In another aspect, the fragrant material can be opaque.

The outer surfaces of the outer housing and/or the capsule can include indicia.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The invention claimed is:
1. An air freshener device, comprising:
a) a housing;
b) a scent capsule carried by the housing and comprising a reservoir containing a fragrant material, and with an opening to a cavity therein and covered by a permeable membrane through which a fragrance can permeate, and a releasable seal removably sealed over the opening and the permeable membrane to resist fragrance release until removed; and
c) a pair of shells pivotally coupled together at a rocker hinge defining a rocker axis, and substantially separated from one another by a gap therebetween;
d) the rocker axis being off-center with respect to the pair of shells and dividing each of the pair of shells at the rocker axis into a long lobe and a short lobe; and
e) the pair of shells rocking about the rocker axis between
i) a low position in which the long lobes of the pair of shells are pivoted substantially together and separating the short lobes of the pair of shell from one another to substantially narrow the gap between the long lobes corresponding to a low scent release, and ii) a high position in which the short lobes of the air of shells are pivoted substantially together and separating the long lobes of the pair of shells from one another to substantially widen the gap between the long lobes corresponding to a high scent release;
f) one of the pair of shells defining an outer shell;
g) an aperture formed in the outer shell;
h) an arc wall formed around at least a portion of the aperture on an interior of the outer shell and defining a pocket;
i) the scent capsule carried by the outer shell and having a vessel defined by the cavity and a perimeter flange circumscribing the vessel and the cavity; and
j) the vessel of the capsule disposed in the aperture of the outer shell with the perimeter flange abutting the outer shell in the pocket and at least partially surrounded by the arc wall.

2. The air freshener device in accordance with claim 1, further comprising:
an absorptive pad disposed between the scent capsule and the housing capable of absorbing the fragrant material that permeates through the permeable membrane.

3. The air freshener device in accordance with claim 2, wherein an amount of fragrant material permeates through the permeable membrane and accumulates between the permeable membrane and the releasable seal defining a leak pool of fragrant material; and wherein the absorptive pad absorbs the leak pool of fragrant material.

4. The air freshener device in accordance with claim 2, wherein the absorptive pad comprises an absorptive material that is fibrous and porous.

5. The air freshener device in accordance with claim 2, wherein the absorptive pad has a perimeter aligned with a perimeter of the reservoir.

6. The air freshener device in accordance with claim 2, wherein the absorptive pad has at least one aperture therethrough located at an interior with respect to a perimeter of the absorptive pad.

7. The air freshener device in accordance with claim 2, wherein the reservoir has a circular perimeter; and wherein the absorptive material pad is annular with a perimeter aligned with the circular perimeter of the reservoir.

8. The air freshener device in accordance with claim 1, wherein:
a) the scent capsule has a vessel defining the cavity and that extends into the aperture of the outer shell;
b) another of the pair of shells defines an inner shell; and
c) mounting means attached to the inner shell for mounting the housing to a support surface.

9. The air freshener device in accordance with claim 8, further comprising:
a pocket in an interior of the outer shell receiving the scent capsule therein; and
a retainer ring holding the scent capsule in the pocket.

10. The air freshener device in accordance with claim 1, further comprising:
a pull tab extending from the releasable seal and extending out of the housing through the gap between the pair of shells.

11. The air freshener device in accordance with claim 2, wherein one of the pair of shells defines an outer shell; wherein the absorptive pad is annular; and further comprising:
a retainer ring holding the scent capsule and the absorptive pad to the outer shell.

12. The air freshener device in accordance with claim 2, further comprising:
a) the absorptive pad being annular with an aperture therein and being disposed against the scent capsule and at least partially surrounded by the arc wall; and
b) a retainer ring disposed against the absorptive pad and holding the scent capsule and the absorptive pad in the pocket, and at least partially surrounded by the arc wall.

13. The air freshener device in accordance with claim 12, further comprising:
a) another of the pair of shells defining an inner shell;
b) a pair of tabs extending from the inner shell;
c) a pair of tabs, each one on the arc wall opposite one another across the pocket of the outer shell; and
d) the pair of tabs of the outer shell aligned with the outer tabs of the inner shell, and about which the pair of shells rock.

14. The air freshener device in accordance with claim 1, wherein:

a) the pair of shells have opposing, spaced-apart inner rims;
b) the rim of at least one of the shells forming a pair of portions about the rocker axis with a long rim associated with the long lobe and a short rim associated with the short lobe; and
c) the long and short rims forming an obtuse angle.

15. A method for providing a fragrance using the air freshener in accordance with claim 2, comprising:
a) removing the releasable seal from the scent capsule with the absorptive pad held against the permeable membrane or a perimeter flange of the scent capsule or both;
b) pushing the upper lobes of the pair of shells together to decrease an amount of scent released; and
c) pushing the lower lobes of the pair of shells together to increase an amount of scent released.

16. A method for providing a fragrance using the air freshener in accordance with claim 2, comprising:
removing the releasable seal from the scent capsule with the absorptive pad held against the permeable membrane or a perimeter flange of the scent capsule or both.

17. An air freshener device, comprising:
a) a housing comprising a pair of shells pivotally coupled together at a rocker hinge defining a rocker axis, and substantially separated from one another by a gap therebetween;
b) the rocker axis being off-center with respect to the pair of shells and dividing each of the pair of shells at the rocker axis into a long lobe and a short lobe;
c) one of the pair of shells defining an outer shell with an aperture therein, while one of the pair of shells defining an inner shell;
d) an arc wall formed around at least a portion of the aperture on an interior of the outer shell and defining a pocket;
e) a scent capsule carried by the housing and comprising a reservoir containing a fragrant material, and with an opening to a cavity therein and covered by a permeable membrane through which a fragrance can permeate, and a releasable seal sealed over the opening and the permeable membrane to resist fragrance release until removed, the scent capsule having a vessel defining the cavity and a perimeter flange circumscribing the vessel and the cavity;
f) the vessel of the capsule disposed in the aperture of the outer shell with the perimeter flange abutting the outer shell in the pocket and at least partially surrounded by the arc wall;
g) an absorptive pad disposed behind the releasable seal capable of absorbing the fragrant material that permeates through the permeable membrane;
h) a retainer ring disposed against the absorptive pad and holding the scent capsule and the absorptive pad in the pocket, and at least partially surrounded by the arc wall;
i) the absorptive pad being annular with an aperture therein, and the absorptive pad has a perimeter aligned with a perimeter of the reservoir;
j) the absorptive pad comprising an absorptive material that is fibrous and porous;
k) the pair of shells having opposing, spaced-apart inner rims;
l) the rim of at least one of the shells forming a pair of portions about the rocker axis with a long rim associated with the long lobe and a short rim associated with the short lobe; and
m) the long and short rims forming an obtuse angle; and
n) the pair of shells rocking about the rocker axis between
i) a low position in which the long lobes of the pair of shells are pivoted substantially together and separating the short lobes of the pair of shell from one another to substantially narrow the gap between the long lobes corresponding to a low scent release, and ii) a high position in which the short lobes of the pair of shells are pivoted substantially together and separating the long lobes of the pair of shells from one another to substantially widen the gap between the long lobes corresponding to a high scent release.

18. An air freshener device, comprising:
a) a housing comprising a pair of shells with cavities facing one another and pivotally coupled together at a rocker hinge defining a rocker axis, and substantially separated from one another by a gap there between;
b) a fragrant material disposed in a cavity of the housing;
c) the rocker axis being off-center with respect to the pair of shells and dividing each of the pair of shells at the rocker axis into a long lobe and a short lobe;
d) the pair of shells rocking about the rocker axis between i) a low position in which the long lobes of the pair of shells are pivoted substantially together and separating the short lobes of the pair of shell from one another to substantially narrow the gap between the long lobes corresponding to a low scent release, and ii) a high position in which the short lobes of the pair of shells are pivoted substantially together and separating the long lobes of the pair of shells form one another to substantially widen the gap between the long lobes corresponding to a high scent release;
e) the pair of shells having opposing, spaced-apart rims; and
f) at least one of the rims having two portions forming an obtuse angle about the rocker axis.

19. The air freshener device in accordance with claim 18, further comprising:
a) a scent capsule carried by the housing and comprising a reservoir containing the fragrant material. and with an opening to a cavity therein and covered by a permeable membrane through which a fragrance can permeate, and a releasable seal sealed over the opening ad the permeable membrane to resist fragrance release until removed; and
b) an absorptive pad disposed behind the releasable seal between the scent capsule and the housing capable of absorbing the fragrant material that permeates through the permeable membrane.

* * * * *